United States Patent [19]
Orejola

[11] Patent Number: 5,618,270
[45] Date of Patent: Apr. 8, 1997

[54] TRANSTHORACIC AORTIC SLEEVE

[76] Inventor: Wilmo C. Orejola, 144 Mountain Ave., Pompton Plains, N.J. 07444

[21] Appl. No.: 452,302

[22] Filed: May 26, 1995

[51] Int. Cl.⁶ .................................................. A61M 5/178
[52] U.S. Cl. ............................ 604/164; 604/167; 604/28; 604/53; 604/174
[58] Field of Search ..................................... 606/108, 185; 604/164, 167, 169, 264, 174, 175, 256, 8, 9, 93, 53, 28; 128/26 D

[56] References Cited

U.S. PATENT DOCUMENTS

| | | | |
|---|---|---|---|
| 3,613,684 | 10/1971 | Sheridan | 604/264 |
| 4,122,858 | 10/1978 | Schiff | 604/175 |
| 4,318,401 | 3/1982 | Zimmerman | 604/167 |
| 5,082,005 | 1/1992 | Kaldany | 604/175 |
| 5,151,087 | 9/1992 | Jonkman | 604/164 |

*Primary Examiner*—Robert A. Hafer
*Assistant Examiner*—Benjamin Koo
*Attorney, Agent, or Firm*—Linval B. Castle

[57] ABSTRACT

For patients requiring intra-aortic balloon (IAB) therapy but cannot take it through the usual femoral artery, it is necessary to open the chest to directly insert the IAB directly to the artery. A new process includes a transthoracic aortic sleeve of teflon or woven dacron tubing 30–40 cm. long formed with a brim at the aortic end and a closed conical exterior end. The conical exterior end is threading through a small incision in the skin and the conical end is then cut off and replaced with a one-way valve. Then a purse string closure is stitched on the adventitial wall of the aorta around the IAB entry point, the sutures of the purse string passing into the sleeve brim. A small incision is then made in the center of the purse string, the IAB is inserted and the purse string tightened and tied. The sleeve prevents blood loss into the chest cavity and keeps all blood loss to a minimum, especially during removal of the IAB.

7 Claims, 3 Drawing Sheets

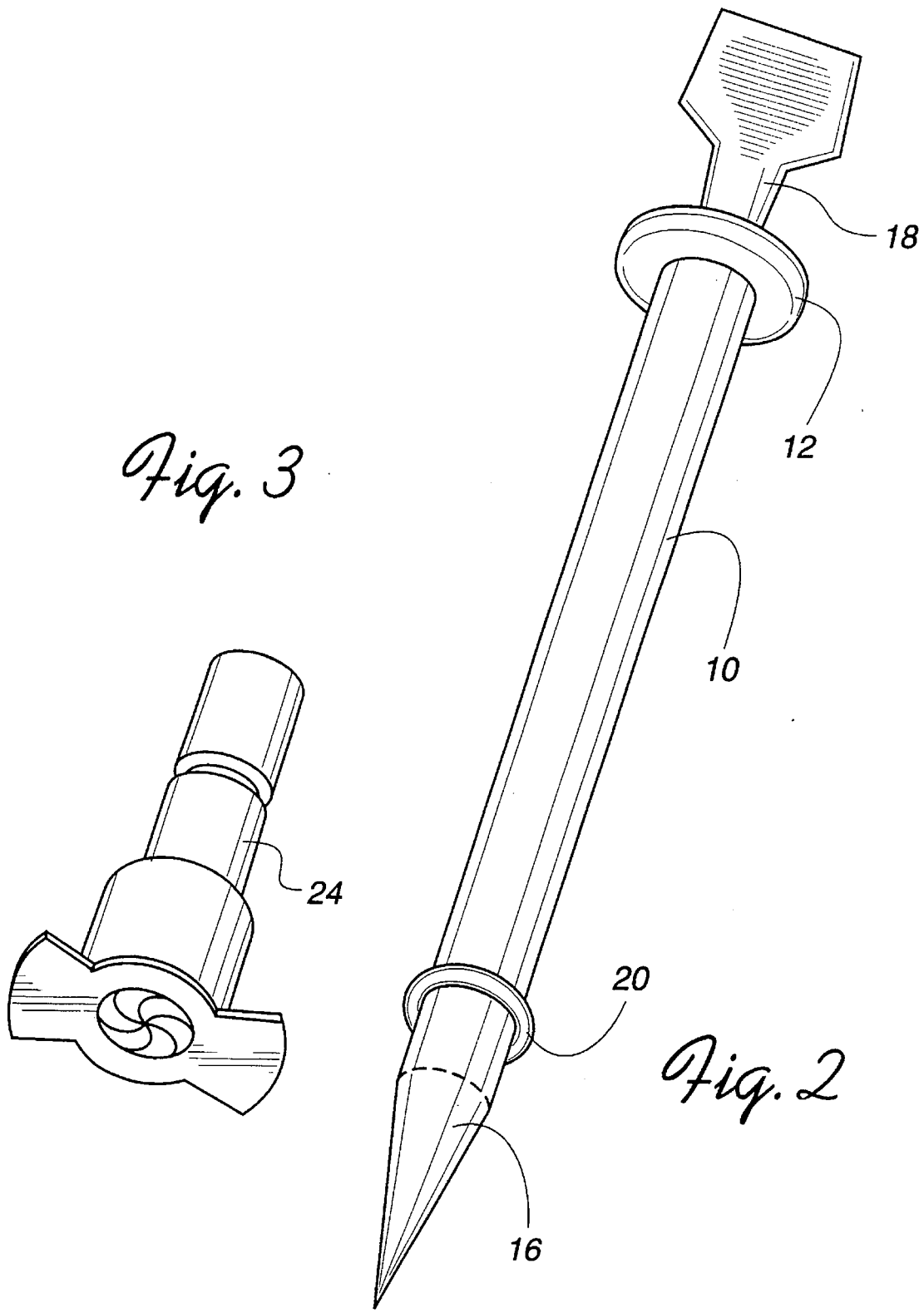

TRANSTHORACIC AORTIC SLEEVE

This invention relates to surgical apparatus and in particular to a transthoracic aortic sleeve and its installation.

BRIEF SUMMARY OF THE INVENTION

As more seriously ill open-heart patients are operated upon, the need for some post-cardiotomy circulatory assistance has increased. The intra-aortic balloon pump is most often resorted to for this purpose; however, this procedure can prove dangerous to patients who have a severe peripheral vascular disease that presents problems for the widely used method of groin insertion of the intra-aortic balloon. Because of this, patients have died in the operating room without the benefit of circulatory assistance simply because of limited access to the balloon insertion.

A more aggressive approach of intra-aortic balloon insertion through the ascending aorta has been attempted by various surgeons at different institutions. While the insertion, per se, is not a problem if done while the chest is open, bleeding is a serious complication the surgeon must contend with since a very tiny leak in the aorta results is a very significant amount of blood loss and a subsequent hemodynamic instability in a critically ill patient.

This invention is for a transthoracic aortic sleeve and the method for its installation for minimizing the problem of blood leakage at the insertion site of an intra-aortic balloon (IAB) or other catheters inserted directly into the aorta. When properly attached to the aorta the sleeve traps blood leaking from the incision site and facilitates removal of the catheter from the aorta with minimum blood loss. The invention also makes it possible to remove the catheter without reopening the patient's chest if the surgeon elects to do so.

The transthoracic aortic sleeve is a tube having a length of 30 to 40 cm. and a diameter of 4 to 8 mm. depending upon the size of the catheter to be used. At the aortic end of the sleeve is a brim reinforced at opposite sides with two small semicircular teflon pledgets. At the opposite or external end the sleeve is tapered and closed and initially contains a stiffener or introducer which facilitates easy insertion of the sleeve from inside to the outside through a small incision in the skin near the lower end of the sternal wound incision. After the insertion the introducer is removed and discarded, the tapered end is cut off and the cut end of the sleeve is fitted and secured with an O-ring to a one-way valve adapter that is later sutured to the skin for stability.

The brim end of the sleeve is then attached to the aorta. Sutures forming a purse string type of closure are first stitched on the outer layer of the wall of the ascending aorta on each side of a selected site for the insertion of an intra-aortic balloon (IAB) catheter, the sutures are fed through the brim and pledgets on the sleeve, and a small incision is made in the aorta in the center of the purse strings, sealing it with a finger for hemostasis. The IAB is pulled from the brim end of the sleeve and inserted through the incision and the purse string are tightened to seal the incision around the inserted IAB catheter.

The transthoracic aortic sleeve and its installation procedure will be more fully understood when considered with the accompanying drawings and the detailed description following their description.

DESCRIPTION OF THE DRAWINGS

In the drawings which illustrate the preferred embodiment of the invention:

FIG. 2 illustrates a transthoracic aortic sleeve prior to use with a conically pointed exterior and with the inserted introducer;

FIG. 3 illustrates a one way valve which is secured to the exterior end of the sleeve by an O-ring.

DETAILED DESCRIPTION OF THE PREFERRED EMBODIMENT

Figure 1:
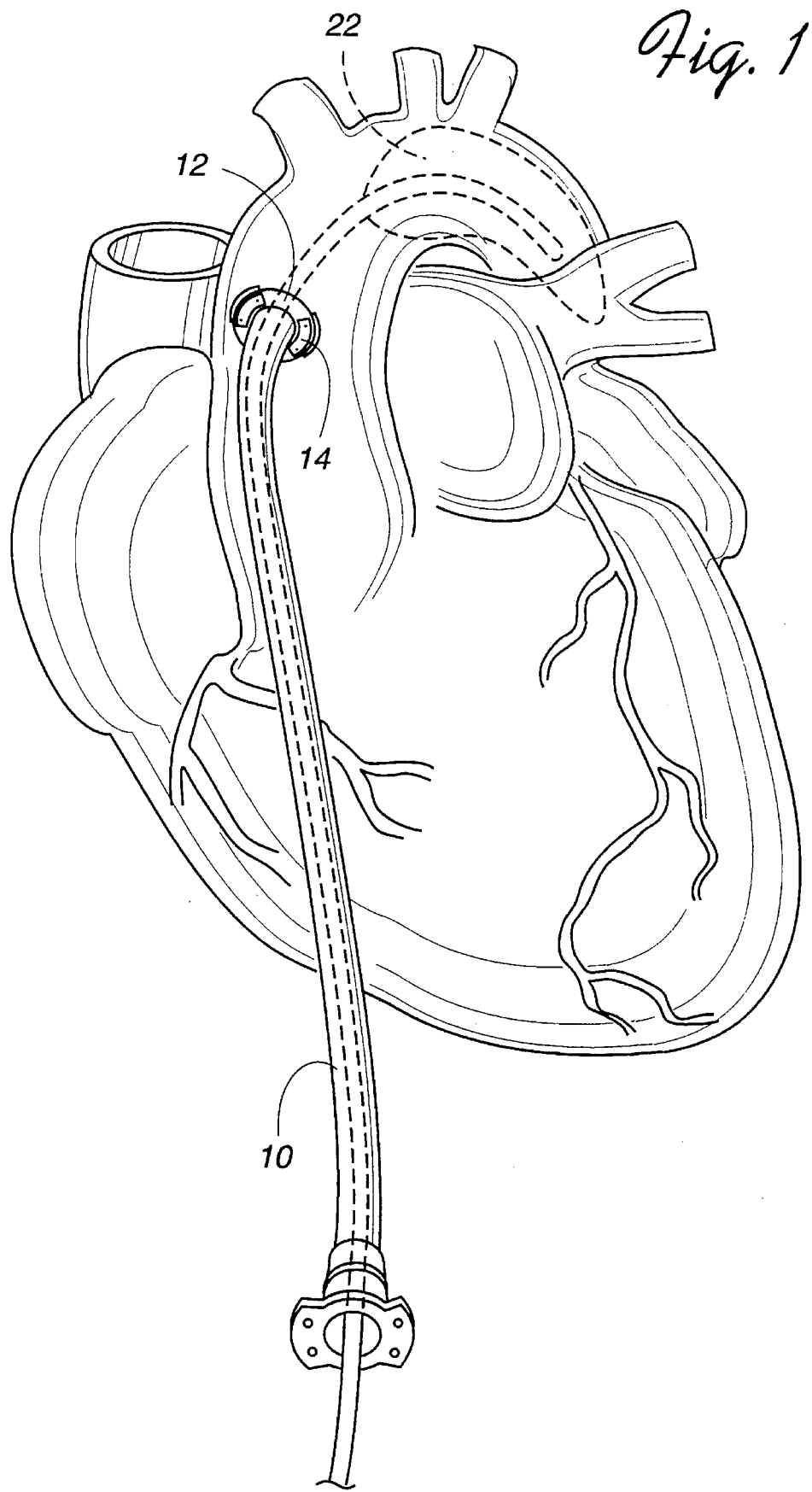
FIG. 1 is a diagram illustrating a human heart with a transthoracic aortic sleeve attached.

The transthoracic aortic sleeve is a surgical appliance to be used in those few cases where a patient must have an inserted catheter such as an intra-aortic balloon (IAB) or a ventricular venting loop catheter that cannot be inserted through the femoral artery at the groi. In such cases it is necessary to take the more aggressive approach of inserting the catheter directly into the aorta. While such an insertion in not a problem when done when the chest is open, bleeding is a serious complication since a very tiny leak in the aorta results in a very significant blood loss in an already critically ill patient.

The transthoracic aortic sleeve 10 is designed to minimize the problem of leakage at the insertion site of a catheter inserted into the aorta since it traps blood that would have leaked into the chest. The sleeve comprises a sterile tubular graft of expanded polytetrafluoroethylene (teflon) or low porosity woven dacron with a uniform inside diameter of about 4 to 8 mm., depending upon the size of catheter used, and a length of approximately 30–40 cm depending upon the height of the patient. The aorta end of the sleeve 10 has a flat disclike brim 12 which extends outward about 6 mm. and which is reinforced on one surface with two opposing teflon semicircular pledgets 14 that serve to anchor and secure the sleeve to corresponding size pledgets that will be carefully stitched to the adventitial wall of the aorta.

The opposite or external end of the aortic sleeve 10 is initially formed in a conically closed point 16 and is adapted to be inserted from inside the skin to the outside through a small incision on the skin near the sternal wound incision at the subxiphoid space. The sleeve is initially provided with a long pencil-shaped introducer 18 or sleeve stiffener which facilitates the sleeve insertion and is then removed and discarded. After insertion of the external end of the sleeve to about half its length, the conical end is cut about half a centimeter down from an O-ring 20 located on the sleeve just above the conical end portion, and a catheter 22 is passed from the outside into the sleeve through a one-way valve adapter 24. The one-way valve adapter 24 has a grooved tubular housing adapted to closely fit around the sleeve 10 and contains a commercially available one-way valve that will admit catheters but will prevent the escape of blood. It is applied over the cut end of the sleeve until the O-ring 20 snaps into the groove. The one-way valve adapter may then be sutured to the skin for stability.

Figure 4:
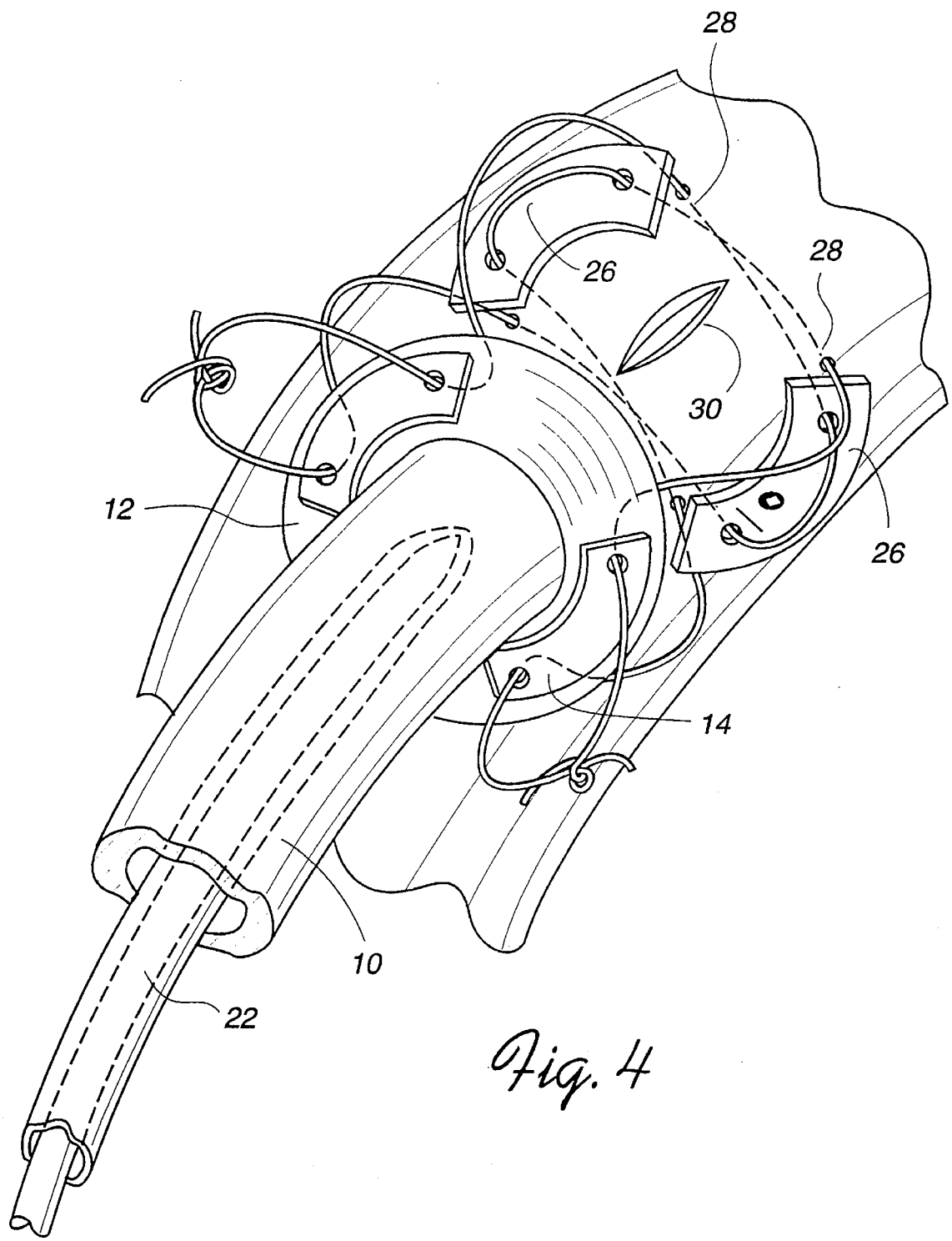
FIG. 4 is a greatly enlarged view of an aorta illustrating the attachment of the brim end of a sleeve over an aortotomy.

Referring now to FIG. 4, two teflon pledgets 26 are carefully stitched in the aortic wall about a half centimeter apart on each side of the selected point of the IAB insertion preferably using two prolene 4-O sutures. Both sutures form a purse string 28. The needles are passed to the contralateral side of the sleeve brim 12 and its reinforcing pledgets 14.

A small incision 30 is made in the aorta between the purse strings 28. This incision is sealed with an index finger for hermostatis until the catheter is drawn from within the sleeve 10 and inserted into the aorta. The purse strings are then tightened to seal the aortotomy around the catheter tubing after establishing the correct position of the catheter and the purse string sutures are tied.

To remove the aortic sleeve, the catheter or intra-aortic balloon is slowly withdrawn from the aorta and, when clear of the aorta, clamp the sleeve near the brim 12, cut the sleeve and remove it. To prevent bleeding through the cut sleeve, oversew the cut end of the sleeve with prolene suture.

In some cases, after removing the IAB through the subxiphoid, the sleeve may be left inside the patient to clot since the external end is closed and sutured under the skin. Leaving grafts inside the chest in this manner has been described in the literature by DeBakey and other workers with ventricular assist devices.

When used as described, the transthoracic sleeve rechannels any bleeding to the outside rather than innocuously inside a patient's chest. A very important advantage in using the sleeve is that it provides a means to safely manipulate aortic removal of an intra-aortic balloon (IAB) from the ascending aorta without much blood loss.

I claim:

1. A thoracic aortic sleeve for providing an insertion path for a catheter or an intra-aortic balloon directly into an aorta, said sleeve comprising;

a sterile tubular member having a length of from 30 to 40 cm. and an inside diameter of from 4 to 8 mm. said member having an aortic end and an exterior end;

a brim consisting of a flat disc perpendicular to the axis of said member, said brim formed in said aortic end of said member, said brim supporting two reinforcing pledgets oppositely located on one surface thereof;

a skin piercing closed end cone formed in said exterior end of said member; and a removable introducer within said member, said introducer having a conical shaped end to conform to said end cone in said member.

2. The aortic sleeve claimed in claim 1 further including a one-way valve, said valve being connected to the exterior end of said member after removal of said introducer and said closed end cone.

3. A procedure for the attachment of a transthoracic aortic sleeve containing a catheter to be inserted into the aorta of a patient while said patient's chest is open, said aortic sleeve including a tubular member having an aortic end with a pledget reinforced brim and an initially closed conical exterior end, said procedure comprising the steps of:

stitching to the aortic wall two lengths of suture forming a purse string around the sides of the selected attachment point of said sleeve;

passing both ends of each of said two sutures through the pledget reinforced brim of said sleeve;

making an incision through the aortic wall sufficiently large to pass the catheter at the selected point of attachment of said sleeve;

passing said catheter through said sleeve and inserting said catheter through said incision into said aorta; and drawing together the ends of each of said two sutures to close the purse string surrounding said incision around said catheter and tying said sutures.

4. The procedure claimed in claim 3 including the preliminary step of passing said closed conical exterior end of said sleeve, from inside to outside the patient's body, through an incision made in the patient's skin.

5. The procedure claimed in claim 4 including the step of removing from said conical closed end an introducer conforming to the interior of said conical closed end, said introducer initially placed in said sleeve to assist in passing said conical end through an incision in the patient's skin.

6. The procedure claimed in claim 5 including the step of removing said conical closed exterior end and adding to the exterior end of said sleeve a one-way valve that admits a catheter but prevents blood from escaping from said sleeve.

7. The procedure claimed in claim 6 including the step of suturing said one-way valve to the skin of said patient.

* * * * *